(12) United States Patent
Schmieding

(10) Patent No.: US 9,700,297 B2
(45) Date of Patent: Jul. 11, 2017

(54) LAMINATED SURGICAL DEVICE

(71) Applicant: ARTHREX, INC., Naples, FL (US)

(72) Inventor: John Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 357 days.

(21) Appl. No.: 14/182,494

(22) Filed: Feb. 18, 2014

(65) Prior Publication Data

US 2014/0243888 A1   Aug. 28, 2014

Related U.S. Application Data

(60) Provisional application No. 61/767,834, filed on Feb. 22, 2013.

(51) Int. Cl.
*A61B 17/04* (2006.01)
*A61B 17/00* (2006.01)
*A61B 17/064* (2006.01)

(52) U.S. Cl.
CPC   *A61B 17/0401* (2013.01); *A61B 2017/00526* (2013.01); *A61B 2017/00831* (2013.01); *A61B 2017/00964* (2013.01); *A61B 2017/0403* (2013.01); *A61B 2017/0414* (2013.01); *A61B 2017/0647* (2013.01)

(58) Field of Classification Search
CPC ........ A61B 17/0401; A61B 2017/0414; A61B 2017/0647; A61B 2017/00831; A61B 2017/00964; A61B 2017/00526; A61B 2017/0403
See application file for complete search history.

(56) References Cited

U.S. PATENT DOCUMENTS

| | | | | |
|---|---|---|---|---|
| 5,458,636 | A * | 10/1995 | Brancato | A61F 2/0063 606/151 |
| 6,083,522 | A * | 7/2000 | Chu | A61B 17/0401 424/423 |
| 6,280,474 | B1 * | 8/2001 | Cassidy | A61B 17/0401 606/232 |
| 6,432,123 | B2 * | 8/2002 | Schwartz | 606/232 |
| 7,226,469 | B2 | 6/2007 | Benavitz et al. | |
| 7,377,934 | B2 | 5/2008 | Lin et al. | |
| 7,862,585 | B2 * | 1/2011 | Li | A61B 17/0401 606/232 |
| 8,012,171 | B2 | 9/2011 | Schmieding | |
| 8,083,768 | B2 * | 12/2011 | Ginn | A61B 17/0057 606/232 |
| 8,231,387 | B2 * | 7/2012 | Salvi | A61C 8/0012 433/174 |
| 8,840,643 | B2 * | 9/2014 | Dreyfuss | A61B 17/0401 606/232 |
| 2004/0193188 | A1 | 9/2004 | Francese | |
| 2005/0228448 | A1 * | 10/2005 | Li | A61B 17/0401 606/232 |
| 2008/0255561 | A1 * | 10/2008 | Tormala | A61L 27/446 606/77 |

\* cited by examiner

*Primary Examiner* — Julian W Woo

(74) *Attorney, Agent, or Firm* — Rubin and Rudman LLP

(57) ABSTRACT

A surgical device according to an exemplary aspect of the present disclosure includes, among other things, a first laminated layer and a second laminated layer fused to the first laminated layer to construct a body portion. At least one of the first laminated layer and the second laminated layer is constructed of a plurality of laminae that are made from a porous material.

18 Claims, 2 Drawing Sheets

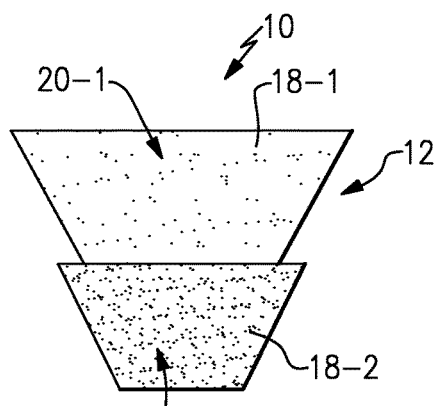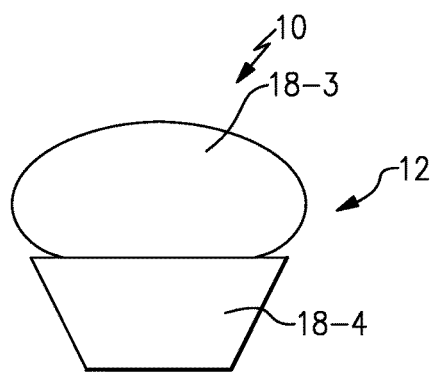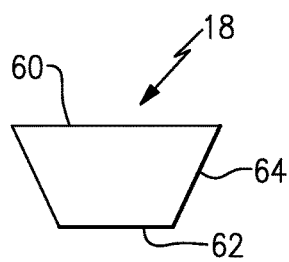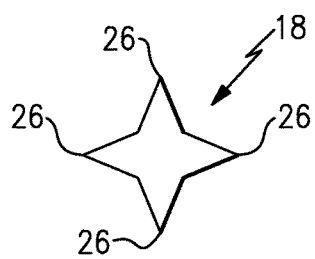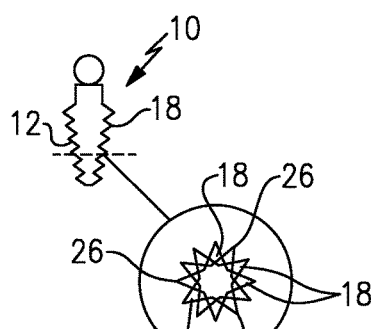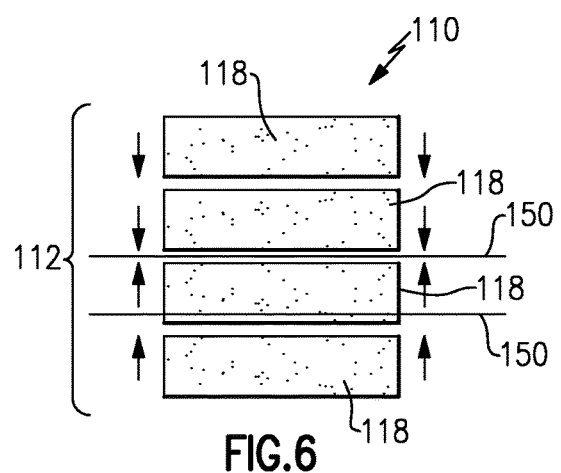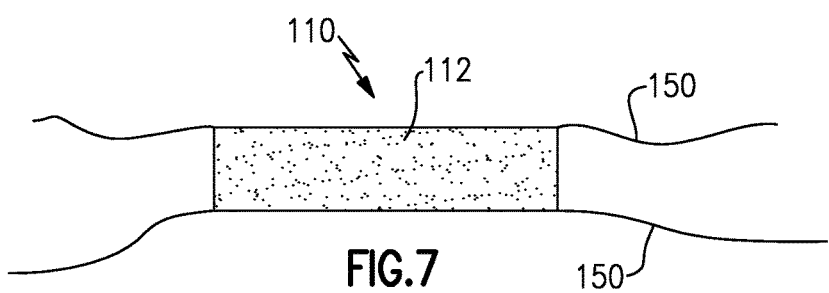

LAMINATED SURGICAL DEVICE

CROSS-REFERENCE TO RELATED APPLICATION

This application claims priority to U.S. Provisional Application No. 61/767,834, which was filed on Feb. 22, 2013.

BACKGROUND

This disclosure relates to a surgical device, and more particularly to a surgical device constructed of a plurality of laminated layers.

Orthopedic procedures are regularly performed to repair musculoskeletal injuries. For example, soft tissue may tear away from bone during vigorous exercise or sporting activities. When these tears occur, reattachment is often necessary to repair the damaged tissue.

Various surgical devices, including sutures, screws, staples, wedges, buttons and plugs, have been used in the past to repair damaged tissue. More recently, various types of suture anchors have been developed for reattaching tissue to bone. Efforts have continued to develop surgical devices that satisfactorily repair damaged tissue and facilitate healing and tissue ingrowth.

SUMMARY

A surgical device according to an exemplary aspect of the present disclosure includes, among other things, a first laminated layer and a second laminated layer fused to the first laminated layer to construct a body portion. At least one of the first laminated layer and the second laminated layer is constructed of a plurality of laminae that are made from a porous material.

In a further non-limiting embodiment of the foregoing surgical device, the surgical device is a suture anchor.

In a further non-limiting embodiment of either of the foregoing surgical devices, the surgical device is surgical tape.

In a further non-limiting embodiment of any of the foregoing surgical devices, the first laminated layer includes a first porous structure having a first porosity and the second laminated layer includes a second porous structure having a second porosity that is different than the first porosity.

In a further non-limiting embodiment of any of the foregoing surgical devices, at least one characteristic of the second laminated layer is dissimilar from the first laminated layer.

In a further non-limiting embodiment of any of the foregoing surgical devices, at least one suture is integrated into the body portion.

In a further non-limiting embodiment of any of the foregoing surgical devices, the at least one suture forms an eyelet.

In a further non-limiting embodiment of any of the foregoing surgical devices, an eyelet is connected to the body portion.

In a further non-limiting embodiment of any of the foregoing surgical devices, at least one of the first laminated layer and the second laminated layer is frustoconical shaped.

In a further non-limiting embodiment of any of the foregoing surgical devices, at least one of the first laminated layer and the second laminated layer is star shaped.

A surgical device according to another exemplary aspect of the present disclosure includes, among other things, a body portion constructed of a plurality of laminated layers and a suture connected to the body portion.

In a further non-limiting embodiment of the foregoing surgical device, the body portion defines an internal bore that accommodates the suture.

In a further non-limiting embodiment of either of the foregoing surgical devices, the suture forms a suture eyelet that extends outside of the body portion.

In a further non-limiting embodiment of any of the foregoing surgical devices, the suture is sandwiched between at least two layers of the plurality of laminated layers.

In a further non-limiting embodiment of any of the foregoing surgical devices, the suture is carried by an eyelet attached to the body portion.

A method according to another exemplary aspect of the present disclosure includes, among other things, fusing together a plurality of laminated layers to form a body portion of a surgical device. At least one the plurality of laminated layers is constructed of a plurality of laminae that are made from a porous material.

In a further non-limiting embodiment of the foregoing surgical method, the fusing step includes melting.

In a further non-limiting embodiment of either of the foregoing surgical methods, the fusing step includes soldering or welding.

In a further non-limiting embodiment of any of the foregoing surgical methods, the method includes embedding a suture inside the body portion during the fusing step.

In a further non-limiting embodiment of any of the foregoing surgical methods, the method includes bonding an eyelet to the body portion.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

BRIEF DESCRIPTION OF THE DRAWINGS

FIGS. 2A and 2B illustrate various features of a laminated surgical device.

FIG. 3 illustrates a laminated layer that can be used to construct a laminated surgical device.

FIG. 4 illustrates another embodiment of a laminated layer.

FIG. 5 illustrates another laminated surgical device.

FIG. 6 illustrates yet another laminated surgical device.

FIG. 7 illustrates the device of FIG. 6 subsequent to a lamination procedure.

DETAILED DESCRIPTION

This disclosure relates to a laminated surgical device that includes a plurality of laminated layers. The laminated layers can be fused, bonded or otherwise attached together to construct surgical devices having porous body portions that promote healing and tissue ingrowth. The laminated layers described herein provide flexibility in constructing surgical devices of a variety of sizes, shapes and configurations in a relatively efficient and cost effective manner. These and other features are discussed in more detail below.

Figure 1A:
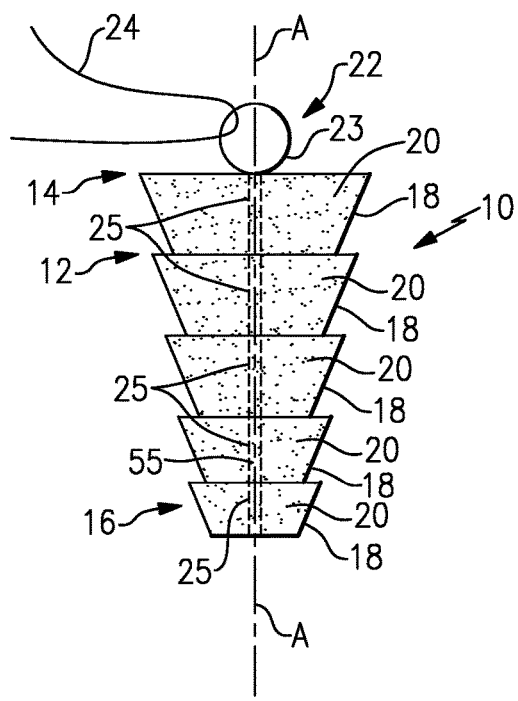
FIGS. 1A, 1B, 1C and 1D illustrate exemplary laminated surgical devices.

FIG. 1A illustrates a surgical device 10. In this non-limiting embodiment, the surgical device 10 is a suture anchor that can be used in an orthopedic procedure to reattach tissue to bone. However, this disclosure is not limited to suture anchors or to procedures involving attachment of tissue to bone. For example, the teachings of this disclosure could extend to other surgical devices that may be used in any procedure, including but not limited to, suture, suture tape, staples, and buttons.

The exemplary surgical device 10 includes a body portion 12 that extend along a longitudinal axis A between a proximal portion 14 and a distal portion 16. The body portion 12 can be made up of a plurality of laminated layers 18. In this disclosure, the term "plurality" denotes two or more. It should be appreciated that the number of laminated layers 18 depicted in FIG. 1A is not intended to be limiting. The laminated layers 18 may be bonded to one another to construct the body portion 12.

In one embodiment, the laminated layers 18 are fused together. One non-limiting fusing technique includes melting the laminated layers 18 together. The laminated layers 18 may be bonded together along the longitudinal axis A in any known manner to construct the body portion 12. Other non-limiting examples of suitable bonding procedures include gluing, soldering, welding and diffusion bonding.

Each laminated layer 18 may have a porous structure 20. The porous structure 20 facilitates tissue and/or bone ingrowth during healing. Exemplary materials that can be used to form the laminated layers 18 include, without limitation, Titanium and PEEK (polyether ether ketone). Other metals and plastics that exhibit porous characteristics may also be selected for use.

Each laminated layer 18 may be constructed of multiple laminae that are made of a porous material. In one embodiment, each laminated layer 18 is constructed layer-by-layer using an additive manufacturing process. However, other procedures may also be utilized to construct the laminated layers 18.

The surgical device 10 may optionally include an eyelet 22. The eyelet 22 can be used to connect a suture 24 to the surgical device 10 to aid in attaching tissue to bone, for example. In this embodiment, the eyelet 22 is positioned at the proximal portion 14 of the body portion 12. However, other locations are also contemplated as suitable eyelet locations within the scope of this disclosure. For example, the eyelet 22 could be disposed at the distal portion 16 of the body portion 12 such as for using the surgical device 10 to achieve knotless fixation of tissue to bone (see FIG. 1B). The suture 24 may be looped through and carried by the eyelet 22.

The eyelet 22 could include a suture eyelet 23. For example, a suture eyelet 23 could be integrally fused, imbedded or otherwise integrated within the body portion 12 at the same time the laminated layers 18 are fused together to form the body portion 12. In another embodiment, the suture eyelet 23 is connected to the body portion 12 by tying a knot in the suture eyelet 23 at either or both of the proximal portion 14 and the distal portion 16. The laminated layers 18 may include one or more passages 25 for accommodating the suture eyelet 23. The passages 25 of each laminated layer 18 align to establish an internal bore 55 through the body portion 12 for accommodating the suture eyelet 23.

One non-limiting example of a suture that can be used to form the suture eyelet 23 is disclosed in U.S. Pat. No. 8,012,171, the disclosure of which is incorporated herein by reference. However, any suture material may be utilized, including any PEEK suture. In yet another non-limiting embodiment, the laminated layers 18 and the suture eyelet 23 are both formed of PEEK material to promote improved fusion between the suture eyelet 23 and the body portion 12.

Figure 1B:
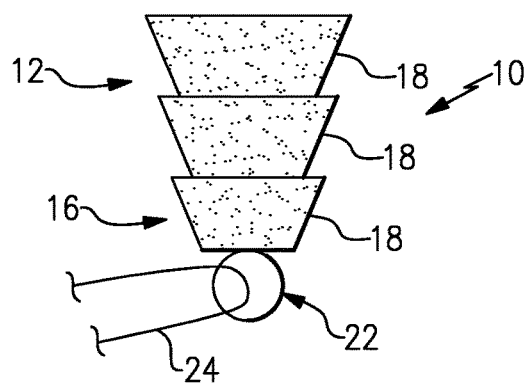
Figure 1C:
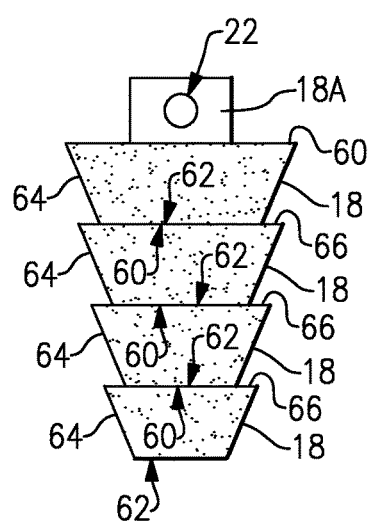
Figure 1D:
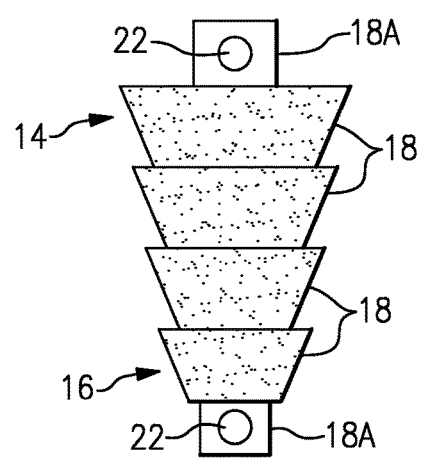

In an alternative embodiment, the eyelet 22 can be provided by using an additional laminated layer 18A (see FIG. 1C). The additional laminated layer 18A may include a different size and shape from the remaining laminated layers 18 that make up the body portion 12. The laminated layer 18A is fused to an adjacent laminated layer 18 at either the proximal portion 14 or the distal portion 16 (or both as shown in FIG. 1D).

FIG. 2A illustrates additional features that may be embodied by the surgical device 10. In this embodiment, the surgical device 10 includes a body portion 12 constructed of at least two laminated layers 18-1 and 18-2 (i.e., first and second laminated layers). The laminated layers 18-1 and 18-2 may include different porosities. For example, the laminated layer 18-1 may include a porous structure 20-1 having a higher porosity compared to a porous structure 20-2 of the laminated layer 18-2, or vice-versa. In this manner, the surgical device 10 can be custom made to accommodate any orthopedic requirement. The porosity characteristics that are incorporated into the body portion 12 of the surgical device 10 can vary depending upon design specific parameters including the type of procedure being performed and tissue quality, among other criteria.

In yet another embodiment, shown in FIG. 2B, the surgical device 10 is constructed using at least two different laminated layers 18-3 and 18-4. In other words, at least one characteristic of the laminated layers 18-3 and 18-4 may be dissimilar. For example, the laminated layer 18-3 may be sized and/or shaped differently than the laminated layer 18-4. In another embodiment, the laminated layer 18-3 is made from a different material than the laminated layer 18-4. Each laminated layer 18 of the body portion 12 of the surgical device 10 can be designed to include or exclude features that are incorporated into the remaining laminated layers 18 that make up the body portion 12.

FIG. 3 illustrates one exemplary laminated layer 18 that can be used to construct the body portion 12 of the surgical device 10 of FIGS. 1A, 1B and 2. In this embodiment, the laminated layer 18 embodies a frustoconical shape. For example, a plurality of circular layers of material of different sizes can be fused together to form the laminated layer 18 having a frustoconical shape. It will be appreciated; however, that the laminated layers 18 may embody any size, shape, and design. In other words, the frustoconical shape depicted by FIG. 3 is intended to be exemplary only.

The laminated layer 18 of FIG. 3 includes a proximal surface 60, a distal surface 62 and a tapering body 64 that extends between the proximal surface 60 and the distal surface 62. In other words, in this embodiment, the laminated layers 18 are truncated cones. Referring again to FIG. 1C (with continued reference to FIG. 3), multiple laminated layers 18 having such a configuration may be stacked relative to one another by positioning the proximal surfaces 60 against the distal surfaces 62 of adjacent laminated layers 18. Fusion of adjacent laminated layers 18 may take place at the interface between the proximal surfaces 60 and the distal surfaces 62.

Positioning the laminated layers 18 in this manner forms a plurality of ledges 66 along the body portion 12. In one embodiment, the ledges 66 are circular ledges that extend circumferentially around at least a portion of the body portion 12. The ledges 66 provide a surface area for receiving backfilled fragments of body tissue during insertion of the surgical device 10 into body tissue. This is referred to as interdigitation. The interdigitation improves fixation of the surgical device 10 within the body tissue.

As shown in the second non-limiting embodiment of FIGS. 4-5, the laminated layers 18 could alternatively be star shaped. A plurality of star shaped laminated layers 18 may be fused together to form another surgical device 10 (see FIG. 5). Each star shaped laminated layer 18 includes a plurality of points 26. In one embodiment, the points 26 of adjacent laminated layers 18 may be circumferentially offset from one another to form body portion 12. In this way, a resilient surgical device may be provided. The points 26 of each laminated layer 18 may aggravate bone during insertion, which may cause bone bleeding to facilitate healing and tissue ingrowth.

The shapes of the laminated layers 18 illustrated in FIGS. 3, 4 and 5 are intended as non-limiting examples of suitable shapes. Other shapes are also contemplated as within the scope of this disclosure.

The surgical devices of FIGS. 1-5 may be implanted into body tissue, including soft or hard body tissue, in order to repair musculoskeletal injuries. In one non-limiting embodiment, the surgical devices of FIGS. 1-5 may be implanted into a hole formed in bone and used to reattach tissue to bone where soft tissue has torn away from the bone. The surgical devices of FIGS. 1-5 could have numerous other applications.

Another exemplary surgical device 110 is illustrated in FIGS. 6 and 7. In this disclosure, like reference numerals designate like features, and reference numerals modified by "100" indicate slightly modified features. In this embodiment, the surgical device 110 is surgical tape that can be used during an orthopedic procedure, such as a wound closure procedure, a cerclage procedure or other similar procedure.

The surgical device 110 includes a body portion 112 made up of a plurality of laminated layers 118. In one embodiment, the laminated layers 118 embody a rectangular shape. However, other shapes are also contemplated. The laminated layers 118 may be fused together to construct the body portion 112. FIG. 6 illustrates the laminated layers 118 before fusion has occurred, and FIG. 7 illustrates the surgical device 110 after fusion has taken place.

The porosity of each laminated layer 118 may be uniform or could be varied. For example, the interior of each laminated layer 118 could include a different porosity than the exterior of each laminated layer 118. The laminated layers 118 can be custom made to accommodate any surgical need. The porosity of the laminated layers 118 allows tissue ingrowth into the surgical device 110.

The surgical device 110 may optionally be constructed to include one or more sutures 150 integrated with the body portion 112. In one non-limiting embodiment, both the laminated layers 118 and the suture 150 are made of a PEEK material to promote better fusion of the suture 150 and the body portion 112. However, other materials may also be utilized. In another non-limiting embodiment, the sutures 150 are sandwiched between at least two laminated layers 118.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A suture anchor, comprising:
a first laminated layer;
a second laminated layer fused to said first laminated layer to construct a body portion;
at least one of said first laminated layer and said second laminated layer is constructed of a plurality of laminae that are made from a porous material that promotes healing and tissue ingrowth, wherein the porous material is metal or polyether ether ketone; and
at least one suture integrated onto said body portion.

2. The suture anchor as recited in claim 1, wherein said first laminated layer includes a first porous structure having a first porosity and said second laminated layer includes a second porous structure having a second porosity that is different than said first porosity.

3. The suture anchor as recited in claim 1, wherein at least one characteristic of said second laminated layer is dissimilar from said first laminated layer.

4. The suture anchor as recited in claim 1, wherein said at least one suture forms an eyelet.

5. The suture anchor as recited in claim 1, comprising an eyelet connected to said body portion.

6. The suture anchor as recited in claim 1, wherein at least one of said first laminated layer and said second laminated layer is frustoconical shaped.

7. The suture anchor as recited in claim 1, wherein at least one of said first laminated layer and said second laminated layer is star shaped.

8. The surgical device as recited in claim 1, wherein said first laminated layer and said second laminated layer are melted together.

9. The surgical device as recited in claim 1, wherein said first laminated layer and said second laminated layer are glued, welded, or soldered together.

10. The surgical device as recited in claim 1, wherein said first laminated layer and said second laminated layer are star shaped, and points of said first laminated layer are circumferentially offset from points of said second laminated layer to form said body portion.

11. The suture anchor of claim 1, wherein the porous material is polyether ether ketone.

12. A surgical device, comprising:
a body portion constructed of a plurality of laminated layers, and each layer of said plurality of laminated layers is melted, glued, welded or soldered to an adjacent layer of said plurality of laminated layers, wherein each layer of said plurality of laminated layers includes porous structure; and
a suture connected to said body portion, wherein the body portion and the suture are formed of polyether ether ketone.

13. The surgical device as recited in claim 12, wherein said body portion defines an internal bore that accommodates said suture.

14. The surgical device as recited in claim 12, wherein said suture forms a suture eyelet that extends outside of said body portion.

15. The surgical device as recited in claim 12, wherein said suture is sandwiched between at least two layers of said plurality of laminated layers.

16. The surgical device as recited in claim 12, wherein said suture is carried by an eyelet attached to said body portion.

17. The surgical device as recited in claim 12, wherein said plurality of laminated layers are melted together to construct said body portion.

18. A surgical device, comprising:
   a body portion extending along a longitudinal axis between a proximal portion and a distal portion, said body portion comprised of a plurality of laminated layers that are glued, soldered, welded or bonded by diffusion together to construct said body portion, and each of said plurality of laminated layers include a porous structure; and
   an eyelet disposed at said proximal portion or said distal portion, said eyelet being connected to said body portion and being provided with an additional laminated layer bonded to said body portion, wherein the body portion and the eyelet are formed of metal or polyether ether ketone.

* * * * *